United States Patent [19]

Artiss et al.

[11] Patent Number: 4,818,691

[45] Date of Patent: Apr. 4, 1989

[54] COLORMETRIC METHOD FOR QUANTIFICATION OF MAGNESIUM USING α-GLYCEROPHOSPHATE OXIDASE

[75] Inventors: Joseph D. Artiss, Windsor, Canada; Bennie Zak, West Bloomfield; Michael C. Wimmer, Lansing, both of Mich.

[73] Assignee: Wayne State University, Detroit, Mich.

[21] Appl. No.: 882,072

[22] Filed: Jul. 3, 1986

[51] Int. Cl.$^4$ ............................ C12Q 1/48; C12Q 1/26
[52] U.S. Cl. .......................................... 435/15; 435/25; 435/28
[58] Field of Search ............................. 435/25, 28, 15

[56] References Cited

U.S. PATENT DOCUMENTS

| | | | |
|---|---|---|---|
| 4,241,178 | 12/1980 | Esders et al. | 435/19 |
| 4,547,461 | 10/1985 | Esders et al. | 435/17 |
| 4,657,854 | 4/1987 | Wegfahrt | 435/14 |

OTHER PUBLICATIONS

*Clinical Chemistry*, vol. 32/4, pp. 629–632, "A Kinetic Colorimetric Procedure for Quantifying Magnesium in Serum", Wimmer et al.

*Primary Examiner*—Sam Rosen
*Attorney, Agent, or Firm*—Arnold S. Weintraub

[57] ABSTRACT

A method and composition for determining magnesium levels in a liquid. The composition contains a first enzyme reagent part having glycerol-kinase, adenosine 5'-triphosphate, 4-aminoantipyrene, α-glycerophosphate oxidase, peroxidase, glycerol kinase, water and a buffer capable of maintaining the solution at a pH between about 5.5 and about 9.2. The composition also contains a second trigger reagent part which has sodium 2-hydroxy-3,5-dichlorobenzene sulfonate, glycerol, water and a buffer capable of maintaining the solution pH between about 5.5 and about 9.2. In the method of the present invention, a liquid to be analyzed is contacted sequentially with the first enzyme reagent part and followed by the second trigger reagent and is measured to quantitatively detect the presence of a detectable species produced as a result of the reactions triggered by the mixture of the enzyme reagent part and the trigger reagent part.

17 Claims, 1 Drawing Sheet

COLORMETRIC METHOD FOR QUANTIFICATION OF MAGNESIUM USING α-GLYCEROPHOSPHATE OXIDASE

BACKGROUND OF THE INVENTION

1. Field of the invention

The present invention relates to the assay of magnesium levels in aqueous liquids. More specifically, the present invention relates to methods for determination of serum magnesium employing α-glycerophosphate oxidase.

2. Background of the Invention

Fast and accurate determination of blood serum quantities and activity levels of various enzymes and minerals is an important medical diagnostic tool. Magnesium is the second most abundant intracellular cation present in the human body and serves as an activator for many important enzymes. Its importance in human physiology is well established. Thus, accurate assay of serum magnesium is an invaluable diagnostic tool.

Numerous spectrophotometric techniques for assaying magnesium have been developed using calmagite, methylthymol blue, titan yellow or Magon sulfonate. These methods have limited accuracy as they are based on chelation reactions and therefore are subject to varying degrees of interference by other cations present in the sample. Atomic absorption and neutron activation analysis are free from these errors, but are very complex and are prohibitively expensive for most routine clinical laboratories.

It has been found that magnesium couples with adenosine diphosphate (ADP) or adenosine triphosphate (ATP) to form a molecular complex. As reported in 31 *Clinical Chemistry*, pp. 703 to 705 (1985), Tabata et al have developed an enzymic magnesium assay using the enzymes hexokinase and glucose-6-phosphate dehydrogenase. In their stopped reaction assay, the amount of (NAD(P)H) produced over a 15 minute period is determined by stoppping the hexokinase reaction with tetrasodium EDTA and measuring the absorbance at 340 nm. This rate-dependent final absorbance is proportional to the amount of Mg.ATP complex present and, hence, to the serum magnesium concentration. This enzymic magnesium assay method requires a sample pre-incubation and prolonged reaction period making it unsuitable for automated instrumental analysis.

The Tabata method has a number of inherent limitations. First, it requires relatively expensive narrow-band spectrophotometers capable of measuring in the ultra-violet region to achieve the true absorbance of the coenzyme indicator. Second, the assay suffers significant interference from lipemia since the light scattering effects of this substance are tremendously enhanced at wavelengths below 400 nm. Third, assay sensitivity is limited due to the relatively low molar absorptivity of the indicator substance employed. Fourth, the assays are plagued by high reagent blanks. Fifth, the necessity to stop the reaction severely reduces the possibility of automating the procedure.

Thus, it would be desirable to develop a method which would yield the fast and accurate determination of magnesium levels in blood serum. It is also desirable to provide a method which would provide a colormetric determination with increased sensitivity. It is also desirable to provide a method which provides detectable results at a wave-length above 340 nm to minimize the light scattering effects of serum turbidity caused in lipemic samples, and places the sample in the visible rather than ultraviolet region of the spectrum.

SUMMARY OF THE INVENTION

A method and associated composition for determining amounts of magnesium present in an aqueous medium is disclosed. The aqueous medium may be any substance of biological or non-biological origin. Examples of these include whole blood, plasma, blood serum, buffered solutions, etc.

This invention is based upon the discovery that the final absorbance produced as a result of the basic reaction in which glycerol is phosphorylated and reacted in the presence of α-glycerophosphate oxidase is rate-dependent and may be made to be proportional to the amount of a complex formed between ATP and magnesium.

The method for determination of magnesium levels in aqueous samples comprises the steps of:

I. contacting a measured amount of the sample with a measured amount of either (a) a reagent solution or (b) solutions containing reagents and enzymes to trigger a sequential reaction which, ultimately, will form a detectable species such as a chromogen; and II. measuring the detectable species thus formed.

The composition of the present invention contains α-glycerophosphate oxidase, peroxidase, glycerol kinase, adenosine-5'triphosphate (ATP), glycerol and specific indicator co-substrates. It has been found that contacting a sample with the enumerated reagents and enzyme composition triggers an ordered series of reactions which are, ultimately, rate-dependent upon the concentration of magnesium present in the sample solution.

The ordered sequence of reactions proceed as follows:

A. magnesium present in the sample interacts with ATP from the reagent solution to form a magnesium-ATP (Mg.ATP) complex;

B. the Mg.ATP phosphorylates glycerol catalyzed by glycerol kinase to form glycerol-3-phosphate and a magnesium-adenosine 5'diphosphate (Mg.ADP) complex, both glycerol and glycerol kinase being contributed by the composition of the present invention;

C. the glycerol-3-phosphate thus produced reacts with environmental oxygen to yield hydrogen peroxide in a reaction catalyzed by the α-glycerophosphate oxidase present in the composition of the present invention; and D. the hydrogen peroxide produced can be measured directly by conventional techniques or reacts further with indicator co-substrates in a peroxidase-catalyzed reaction to from a visually detectable chromogen; the co-substrates and peroxidase present in the composition of the present invention.

For a more complete understanding of the present invention, reference is made to the following detailed description and accompanying examples.

DETAILED DESCRIPTION OF THE INVENTION

Figure 1:
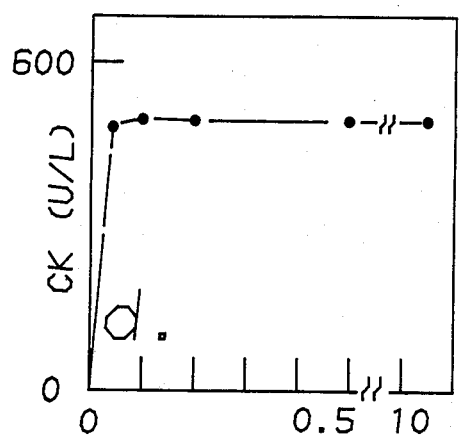
Figure 2:
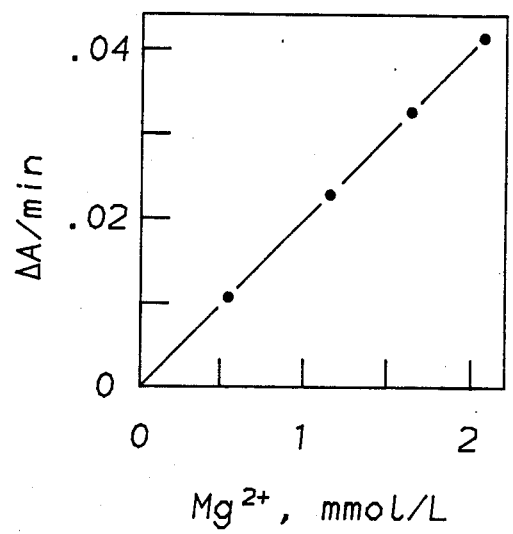
Figure 3:
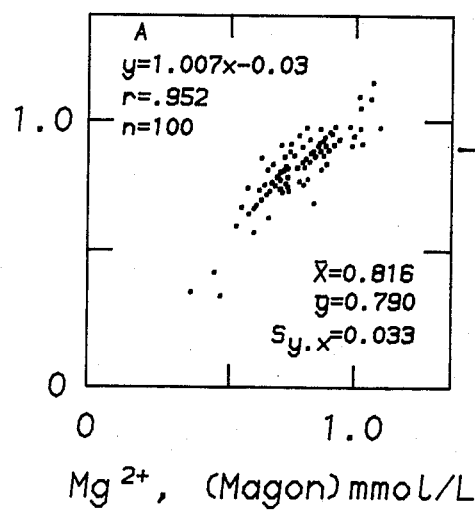
Figure 3:
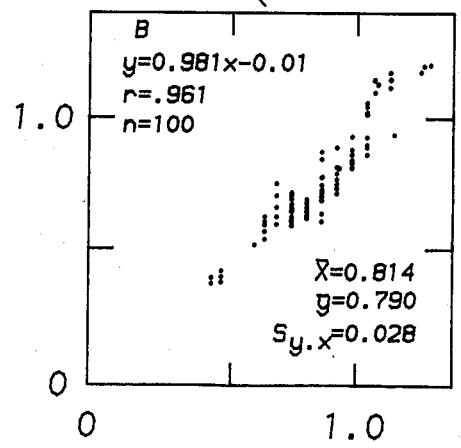

This invention is based upon the discovery that magnesium present in biological fluids has an affinity for, and will complex with, adenosine polyphosphates. It was also found that the rate of the reaction sequence outlined in Table I was dependent upon the complexation of magnesium with ATP; not just the presence of ATP alone. Thus, the Mg.ATP complex forms the limiting reagent in the formation of glycerol-3-phosphate and all subsequent reactions in the sequence.

Thus, the method for determination of magnesium levels in an aqueous sample comprises the steps of:

I. contacting a measured amount of sample with a predetermined amount of either (a) a reagent solution or (b) solutions containing reagents and enzymes to trigger the sequential reaction which, ultimately, forms a detectable species such as a chromogen; and II. measuring the detectable species thus formed.

The ordered sequence of reactions proceeds such that magnesium present in the sample is complexed with ATP. The Mg.ATP complex contributes a phosphate group in the glycerol-kinase-catalyzed phosphorylation of glycerol to glycerol-3-phosphate. Glycerol-3-phosphate in the presence of environmental oxygen and α-glycerophosphate oxidase reacts to form hydrogen peroxide which can be converted to a detectable chromogen through a peroxidase-catalyzed reduction.

In order to perform the method of the present invention, a reagent composition is provided which contains all the reagents and enzymes required to complex to sample magnesium to initiate and sustain the reaction sequence in Table I. The reagent composition can be a one-part solution or a multi-part solution as is desired. The reagent composition consists essentially of:

(a) glycerol kinase;
(b) α-glycerophosphate oxidase;
(c) a compound having peroxidase activity;
(d) adenosine 5'-triphosphate;
(e) glycerol;
(f) a peroxidase oxidizable co-substrate;
(g) an indicator co-substrate coupler;
(h) a buffer capable of maintaining a solution pH between about 5.5 and about 9.2; and
(i) water.

It is within the purview of this invention to add chemicals and enzymes individually or in any combination which will trigger the reaction sequence outlined in Table I. Thus, alternatively, various chemicals and enzymes can be maintained in separate buffered solutions and employed as required. In one embodiment, glycerol and the indicator co-substrate are maintained in a buffered solution separate from a buffered solution containing the remaining constituents. In this embodiment, the solution containing the remaining constituents is admixed with the sample to permit the formation of the Mg.ATP complex. The reagents and sample are allowed to react at a temperature between about 25° C. and about 45° C. for a period between about five seconds and about ten minutes. To ensure intimate contact, the mixture can be agitated. The buffered glycerol solution is, then, added to the mixture. The addition of glycerol will trigger the ordered reaction sequence and permit assay of the sample magnesium concentration.

TABLE I

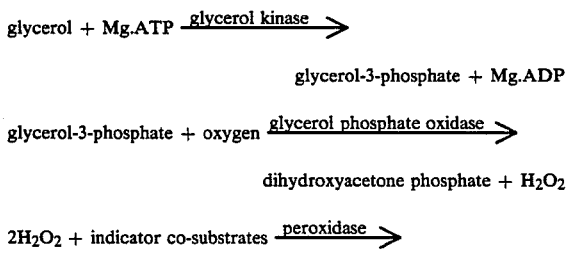

TABLE I-continued colored chromogen + H₂O

Once all of the components are admixed with the sample, the absorbance of the resulting mixture is monitored for an interval of up to about 5 to about 15 minutes at a specified wave-length, between about 450 and about 650 nm preferably at about 510 nm depending upon the indicator co-substrates used. A reagent blank containing a measured amount of water can also be prepared to determine the basic abosrbance of the water used in preparing the reagent solutions. The change in absorbance over time ($\Delta A$/min) is proportional to the magnesium concentration of the sample.

The composition of the present invention contains ATP at a concentration between about 0.05 and about 2.0 millimoles per liter. ATP within this concentration range will complex with magnesium present in a sample of biological fluid to provide efficient determination of sample magnesium levels up to about 2.5 millimoles of magnesium per liter. Magnesium concentrations greater than 2.5 millimole/liter can be determined by measured dilution of the sample with conventional magnesium-free normal saline solutions and reassaying. Suitable ATP is commercially available from Sigma Chemical Corp., St. Louis, Mo.

Once the Mg.ATP complex has formed in the aqueous solution, contact with glycerol in the presence of glycerol kinase will result in the phosphorylation of glycerol to form glycerol-3-phosphate and Mg.ADP. In the method and composition of the present invention, glycerol is employed in a concentration between about 0.05 and about 20 millimoles per liter, with concentrations between about 0.2 about 7 millimoles per liter being preferred. Glycerol can be obtained commercially from Sigma Chemical Co., St. Louis Mo.

In general, glycerol kinase from any source may be used in the successful practice of the present invention although glycerol kinase derived from *Streptomyces canus* (E.C. 2.7.1.30) is preferred. This glycerol kinase can be obtained from Finnsugar Biochemicals, Inc. in Elk Grove Village, Ill. In the present method, glycerol kinase in quantities ranging from about 10 U to about 150 U per liter of buffer are successfully employed.

The glycerol-3-phosphate produced as from the enzyme-catalyzed reaction of Mg.ATP with glyercol reacts in the presence of the enzyme α-glycerophosphate oxidase to form dihydroxyacetone and hydrogen peroxide.

The α-glycerophosphate oxidase employed may be derived from a variety of microbial species which can be derived from a variety of sources. The properties of this enzyme derived from certain sources are more desirable than from others in the method of the present invention. Enzyme obtained from *Aerococcus viridans* is preferred as demonstrating greater activity over a broader pH range than enzyme obtained from other sources. Alpha-glycerophosphate oxidase obtained from this source can be successfully used in the present invention in quantities ranging between about 2.0 kU and about 10.0 kU per liter. For handling ease, the α-glycerophosphate oxidase can be present in the initial solution containing the ATP.

In order to quantify the products formed by the reaction sequence initially triggered by creatine kinase, the hydrogen peroxide produced is measured directly or may be further reacted to form a detectable chromogen in a reaction catalyzed by a peroxidase or a substance having peroxidative activity.

Peroxidases are conjugated proteins containing iron porphyrin. Peroxidases which occur in horseradish, potatoes, fig tree sap, turnips, milk, white blood corpuscles and microorganisms can be successfully employed in the present invention. Certain synthetic peroxidases, such as disclosed by Theorell and Machly in Acta Chem. Scand., Vol. 4, pages 422–434 (1950), are also satisfactory. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes but which possess peroxidative activity which can be employed in the present invention are: iron sulfocyanate, iron tannate, ferrous ferrocyanide, chromic salts (such as potassium chromic sulfate) absorbed in silica gel, etc. These substances are not as satisfactory as peroxidase per se but are similarly useful.

In the method of the present invention, peroxidase derived from horseradish (E.C. 1.11.1.7) obtainable from Finnsugar Biochemicals is preferred. In the method of the present invention, peroxidase enzyme quantities between about 0.5 kU and 20 kU per liter can be employed.

Where the hydrogen peroxide produced is immediately reduced in the presence of a peroxidase it is reacted with a peroxidase-oxidizable substrate or cosubstrate and a coupler-cosubstrate to yield a detectable chromogen. The peroxidase and peroxidase-oxidizable cosubstrate are preferably present in the buffered ATP solution. The coupler cosubstrate may be the present in the glycerol-containing solution to minimize non-specific autocoupling or auto-oxidation during storage.

The peroxidase-oxidizable co-substrates which can be successfully employed are generally those which will react to form a detectable chromogen. The peroxidase oxidizable co-substrate is capable of undergoing oxidative condensation with couplers such as those containing phenolic groups. Representative of such oxidizable compounds are benzidene and its homologs, p-phenylenediamines, p-aminophenols, 4-aminoantipyrine, 3-methyl-2-benzothiazolimone hydrazone, etc., and mixtures thereof.

The coupler-cosubstrate is selected from the group consisting of the ammonia or alkali metal salt of 2-hydroxy-3,5-dichlorobenzenesulfonate (HDCBS), or other aromatic alcohols, amines and mixtures thereof. Preferably, the coupler cosubstrate is HDCBS present in a concentration between about 0.1 millimoles and about 0.5 millimoles per liter.

The chromogen which results from the coupling of HDCBS and 4-aminoantipyrene is a stable red-colored molecule having radiation absorbance in the visible range, between about 450 and 525 nm with a maximum at 510 nm. It has been found that the molar absorptivity of the resulting chromogen is four times that of conventional indicators. The use of the longer wavelength has the added advantage of minimizing the light scattering effects caused by turbidity in lipemic samples.

The reaction sequence optimally occurs at a pH between about 5.5 and about 9.2. Thus, buffering agents may be employed in the composition of the present invention to maintain the pH in this desired range and preferably between about 6.5 and about 7.2.

The buffering agent employed must be one which will not interfere with the reaction sequence of Table I. Suitable buffers include N,N-bis-(2-hydroxyethyl)-2-amino-ethane-sulfonic acid (BES); 3-(N-morpholino)-2-hydroxypropanesulfonic acid (MOPSO); 3-N-morpholinopropanesulfonic acid (MOPS); N-(2-acetamido)-2-aminoethanesulfonic acid (ACES); piperazine-N,N-bis(2-ethanesulfonic acid) (PIPES); 1,3-bis[tris(hydroxymethyl)methylamino]propane(bis-tris propane), tris-(hydroxymethyl)-aminomethane/hydrochloric acid (Tris/HCl), imidazole/hydrochloric acid, alkali phosphate, imidazole/hydrochloric acid or mixtures thereof. Preferably, Tris/HCl is employed at a concentration to yield between about 0.01 and about 1.0 moles per liter in the composition of the present invention.

In order to further illustrate and explain the present invention, the following examples are provided. These examples are intended to be used for illustrative purposes only and are not to be considered limitative of the present invention.

EXAMPLE I

Determination of Magnesium Concentration

A series of magnesium working standards were prepared having concentrations of 0.5, 1.0, 1.5 and 2.0 mmol/L were prepared by appropriate dilution of a 10 mmol/L stock solution of magnesium acetate.

In order to derive a graph of Mg++ concentration versus the change in absorbance over time, each working solution was analyzed according to the following method.

A 0.9 ml portion of the Mg.ATP reagent outlined in Table IIA was introduced into a 12×75 mm test tube and incubated in a 37° C. water bath for 2 to 3 minutes. A 5.0 μL amount of the solution to be analyzed was introduced to the tube and vortex mixed. A 0.1 ml portion of the glycerol solution set forth in Table IIB (preheated to 37° C.) was then added and vortex mixed. The contents were then transferred to a cuvette and the absorbance change at 510 nm was measured for 1 to 10 minutes versus a reagent blank containing 5.0 μL of water. Absorbances were measured on a Gilford model 300-N flow-through spectrophotometer.

The remaining standards and samples were similarly tested and the change in absorbance over time is shown on the graph found in FIG. I. Linear regression analysis of the typical standard curve in FIG. II of four standards in triplicate for 0 to 2 mmol/L Mg++ yielded the equation:

$$y = 0.0195x + 0.00125, r = 0.9988$$

EXAMPLE II

Serum samples were collected and prepared for analysis within 24 hours of collection. Sera were removed from clots within 10 minutes of centrifugation to prevent false elevation of serum magnesium from sequestered erythrocytes. Visibly hemolyzed serum samples were discarded.

Each sample was tested according to the procedure outlined in Example I. The change in absorbance over time was calculated for each sample from the linear portion of the curve. It was found that, following a 2 to 3 minute leg phase, the reaction rates were linear for at least 10 minutes. The assay itself was linear to a magnesium concentration of at least 2.0 mmol/L. Magnesium concentrations greater than that can be diluted with magnesium-free normal saline and successfully reassayed.

TABLE II

Components in Reagents for Determination of Magnesium Concentration

| | Compound | Concentration |
|---|---|---|
| A. Mg ATP Reagent | Tris/HCl buffer | 100 mmol/L |
| | 4-aminoantipyrene | 1.0 mmol/L |
| | adenosine 5'-triphosphate | 0.3 mmol/L |
| | glycerophosphate oxidase | 5 kU |
| | peroxidase | 1 kU |
| | glycerol kinase | 25 U |
| | water | balance |
| B. Glycerol Reagent | Tris/HCl buffer | 100 mmol/L |
| | sodium 2-hydroxy-3,5-dichlorobenzenesulfonate | 1.0 mmol/L |
| | glycerol | 5 mmol/L |
| | water | balance |

EXAMPLE III

One hundred patient sera samples were analyzed by both the present method and by a methylthymol blue method as applied to the DuPont ACA analyzer and to a manual magnon sulfonate method as outlined in Baginski et al, Magnesium in Biological Fluids, *Selected Methods of Clinical Chemistry*, Vol. 19 (1982) pp 277-281 and Baginski et al, Microdetermination of Magnesium in Biological Fluids, 27 *Microchem* (1982) pp 141-150 herein incorporated by reference.

The sample data were compared. Excellent correlation data were obtained with both methods as set forth in FIG. III. Appropriate linear regression data are:

proposed
$(y)=0.981(ACA)-0.01(mmol/L), (r=0.961)$ proposed
$(y)=1.007(magon)-0.03(mmol/L), (r=0.952)$

What is claimed is:

1. A composition for determining magnesium levels in an aqueous fluid having adenosine-5'-triphosphate, water and a buffer capable of maintaining a solution pH between about 5.5 and 9.2, the improvement which comprises in addition:
   glycerol kinase;
   α-glycerophosphate oxidase;
   a substance having peroxidase activity;
   glycerol
   a peroxidase oxidizable co-substrate;
   an indicator co-substrate coupler;
   an acid base buffer capable of maintaining a solution pH between about 5.5 and about 9.2; and
   water.

2. The composition of claim 1 wherein the buffer is tris(hydroxymethyl)aminomethane-hydrochloric acid.

3. The composition of claim 2 wherein the composition comprises two aqueous reagent solutions, the first reagent solution consisting essentially of:
   between about 0.01 and about 1.0 moles of the buffer per liter of water;
   between about 0.05 and about 2.0 millimoles of adenosine-5'-triphosphate per liter of water;
   between about 0.05 and about 10 millimoles of the peroxidase oxidizable co-substrate per liter of water;
   between about 1kU and about 10 kU α-glycerophosphate oxidase per liter of water;
   between about 0.5 kU and about 20 kU per liter of water of the substance having peroxidative-activity; and
   between about 10 U and about 150 U glycerol kinase per liter of water.

4. The composition of claim 3 wherein the second reagent solution consists essentially of:
   between about 0.05 and about 1 moles of buffer per liter of water;
   between about 0.01 and about 5.0 millimoles the indicator cosubstrate coupler per liter of water; and
   between about 0.05 and about 20.0 millimoles of glycerol per liter of water.

5. The composition of claim 1 wherein the peroxidase oxidizable cosubstrate is selected from the group consisting of benzidene, p-phenylenediamines, p-aminophenols, 4-aminoantipyrene, 3-methyl-2-benzothiazolimone, and mixtures thereof.

6. The composition of claim 1 wherein the indicator cosubstrate coupler is selected from the group consisting of ammonia salts of 2-hydroxy-3,5-dichlorobenzenesulfonate, alkali metal salts of 2-hydroxy-3,5-dichlorobenzenesulfonate, and mixtures thereof.

7. The composition of claim 1 wherein the glycerol kinase is magnesium dependent and is derived of *Streptomyces canus*.

8. The composition of claim 1 wherein the glycerol kinase is magnesium dependent and is derived from *Bacilus Stearothemophilis*.

9. The composition of claim 1 wherein the α-glycerophosphate oxidase is derived from *Aerococcus viridans*.

10. A method for determining magnesium in a liquid sample comprising the steps of:
    (a) contacting a sample of the aqueous liquid with a composition consisting essentially of:
        (1) glycerol kinase;
        (2) α-glycerophosphate oxidase;
        (3) peroxidase
        (4) adenosine-5'-triphosphate;
        (5) glycerol;
        (6) a peroxidase oxidizable co-substrate;
        (7) an indicator co-substrate coupler;
        (8) a buffer capable of maintaining a solution pH between about 6.0 and about 8.0; and
        (9) water; and
    (b) quantitatively detecting the presence of magnesium by a reaction product formed in (a), wherein the reaction product is hydrogen peroxide.

11. The method of claim 10 wherein the reaction product is a colored chromagen having an absorbance between about 450 and about 650 mm.

12. The method of claim 11 further comprising the step of observing the formation of the reaction product over a period of up to about 5 to 15 minutes.

13. The method of claim 10 wherein the contacting step occurs at a pH between about 6.5 and about 7.5.

14. The method of claim 10 wherein the composition employed in the contacting step is a two-part reagent solution comprising:
    a first reagent solution consisting essentially of glycerol kinase, adenosine 5'-triphosphate, the peroxidase oxidizable cosubstrate, α-glycerophosphate oxidase, a substance having peroxidative activity, glyercol kinase, water and a buffer capable of maintaining the pH between about 6.0 and about 8.0; and a second reagent solution consisting essentially of the indicator co-substrate coupler, glycerol, water and a buffer capable of maintaining the solution pH between 6.0 and 8.0.

15. The method of claim 14 wherein the first reagent solution consists essentially of:
 (a) water;
 (b) adenosine 5'-triphosphate in an amount ranging between about 0.1 and about 1.0 millimoles per liter of water;
 (c) 4-aminoantipyrene in an amount ranging between about 0.5 and about 2.0 millimoles per liter of water;
 (d) α-glycerophosphate oxidase in an amount ranging between about 2.0 and about 10 U/L;
 (e) peroxidase in an amount ranging between about 0.5 kU and about 2 kU/L;
 (f) glycerol kinase in an amount ranging between about 10 U and about 35 U/L; and
 (g) a buffering agent in a sufficient amount to maintain the pH between about 6.0 and about 8.0.

16. The method of claim 15 wherein the second reagent solution consists essentially of:
 (a) water;
 (b) sodium 2-hydroxy-3,5-dichlorobenzenesulfonate in an amount ranging between about 0.05 and about 2.0 millimoles per liter of water;
 (c) glycerol in an amount ranging between about 0.2 and 10 millimoles per liter; and
 (d) a buffering agent in a sufficient amount to maintain the pH between about 6.0 and about 8.0.

17. The method of claim 16 wherein the contacting step comprises the steps of:
 incubating a measured portion of the first reagent solution at a temperature between about 20° C. and about 45° C.;
 adding a measured sample of the liquid to be assayed;
 admixing the two materials; and
 adding a measured portion of the second reagent solution.

* * * * *